United States Patent
Bovero et al.

(10) Patent No.: US 10,443,787 B2
(45) Date of Patent: Oct. 15, 2019

(54) SYSTEM AND METHOD FOR ENCODING PIPELINE WELDS

(71) Applicant: Saudi Arabian Oil Company, Dhahran (SA)

(72) Inventors: Enrico Bovero, North Vancouver (CA); Gasan Selman Alabedi, Dhahran (SA); Majed F. Al Rajeh, Riyadh (SA); Ali F. Al Qabani, Riyadh (SA)

(73) Assignee: SAUDI ARABIAN OIL COMPANY, Dhahran (SA)

( * ) Notice: Subject to any disclaimer, the term of this patent is extended or adjusted under 35 U.S.C. 154(b) by 192 days.

(21) Appl. No.: 15/715,451

(22) Filed: Sep. 26, 2017

(65) Prior Publication Data
US 2019/0093828 A1   Mar. 28, 2019

(51) Int. Cl.
| | |
|---|---|
| F17D 5/00 | (2006.01) |
| F16L 55/18 | (2006.01) |
| F16L 13/02 | (2006.01) |
| B23K 31/12 | (2006.01) |
| G06Q 10/00 | (2012.01) |
| G01S 19/42 | (2010.01) |

(Continued)

(52) U.S. Cl.
CPC ............ *F17D 5/00* (2013.01); *B23K 31/125* (2013.01); *F16L 13/0272* (2013.01); *F16L 55/18* (2013.01); *G06Q 10/20* (2013.01); *F16L 2201/60* (2013.01); *G01N 23/20* (2013.01); *G01N 2223/628* (2013.01); *G01N 2223/629* (2013.01); *G01S 19/42* (2013.01); *G06K 7/1421* (2013.01); *G06K 19/06168* (2013.01)

(58) Field of Classification Search
CPC ....... F17D 5/00; B23K 31/125; F16L 13/0272
See application file for complete search history.

(56) References Cited

U.S. PATENT DOCUMENTS

| | | | | |
|---|---|---|---|---|
| 4,255,641 A | * | 3/1981 | Connell | B23K 33/006 219/137 R |
| 4,958,857 A | * | 9/1990 | Sixsmith | B29C 66/5221 219/544 |

(Continued)

OTHER PUBLICATIONS

International Search Report and Written Opinion in corresponding International Patent Application No. PCT/US2018/047676 dated Jan. 8, 2019. 15 pages.

*Primary Examiner* — Anand P Bhatnagar
(74) *Attorney, Agent, or Firm* — Leason Ellis LLP

(57) ABSTRACT

Systems and methods are provided for physically labeling structural features, such as weld joints in a pipeline, with pattern-based codes that uniquely identify respective features. The systems and methods are also provided for identifying the features based on imagery of the codes captured during subsequent inspection of the weld joints. In particular, the weld joints can be uniquely identified by encoding measured geographic coordinates within two distinguishable circular patterns that correspond to latitude and longitude, respectively. In addition, the pattern-based codes can be applied to respective weld joints using a contrast material such that the codes are revealed in the images of the weld joints captured during inspection. Furthermore, the systems and methods include analyzing the images captured during inspection to identify the inspected weld joints for the purpose of verifying that each weld joint was properly inspected in the field.

17 Claims, 10 Drawing Sheets

(51) Int. Cl.
*G01N 23/20* (2018.01)
*G06K 7/14* (2006.01)
*G06K 19/06* (2006.01)

(56) References Cited

U.S. PATENT DOCUMENTS

| | | | |
|---|---|---|---|
| 5,491,637 A | 2/1996 | Kraemer et al. | |
| 7,918,387 B2* | 4/2011 | Kahn | D05C 11/00 |
| | | | 235/375 |
| 9,724,787 B2* | 8/2017 | Becker | G09B 19/24 |
| 10,204,406 B2* | 2/2019 | Becker | B23K 9/0953 |
| 10,210,773 B2* | 2/2019 | Becker | G09B 19/24 |
| 2003/0058991 A1* | 3/2003 | Lott | G01N 23/04 |
| | | | 378/60 |
| 2006/0202480 A1* | 9/2006 | Cassel | F01N 13/1805 |
| | | | 285/408 |
| 2014/0326507 A1* | 11/2014 | Spriggs | E21B 17/006 |
| | | | 175/40 |
| 2016/0039034 A1* | 2/2016 | Becker | A61F 9/06 |
| | | | 219/137 R |
| 2016/0125763 A1* | 5/2016 | Becker | B23K 9/126 |
| | | | 434/234 |
| 2016/0288236 A1* | 10/2016 | Becker | B23K 9/0953 |

\* cited by examiner

SYSTEM AND METHOD FOR ENCODING PIPELINE WELDS

FIELD OF THE INVENTION

The present invention relates to pattern-based coding systems and, in particular, relates to a system and method for physically labeling pipeline weld joints with a pattern-based codes that uniquely identify the weld joints.

BACKGROUND OF THE INVENTION

Pipeline structures used in the oil and gas industry typically comprise a series of sections of pipe that are welded together. In operation, portions of the pipeline including the weld joints are periodically inspected to monitor the structural integrity of the pipeline.

Inspection of weld joints is commonly performed by a radiographic technician that images each joint in the field using a digital radiography inspection device so that the images can be inspected to monitor the integrity of respective joints. The images can also be inspected to ensure compliance with inspection requirements, namely, to verify that the technician inspected each joint in the pipeline structure. Because the inspection process can be arduous, a problem in the art is that technicians might be tempted to skip joints in order to complete the inspection more quickly. As such, a radiographic technician might present images of the same joint multiple times for structural analysis and compliance review, as if they were different joints.

Existing methods for addressing this problem of technicians spoofing inspection images include applying letters near each weld joint, either by painting the letter directly onto the pipe surface or applying a letter sticker. The letters can be applied using a contrast material so that the letter appears in the images captured using the inspection device. The imagery and the letters therein can thus be inspected to differentiate between weld joints and verify compliance. However, this system and approach by itself does not prevent tampering because the radiographic technician can digitally replace the letters in the images or replace the physical stickers provided near the weld joints.

Accordingly, there is a need for systems and methods for labeling weld joints of a pipeline structure in a manner that 1) is visually revealed in the output of the inspection device (e.g., scatters x-ray photos so the label is shown in the digital radiographic image of the pipe joint); 2) cannot be separated from the joint and replaced by another label; and 3) uses an information encoding methodology that is intelligible to a radiographic technician and, thus, cannot be spoofed easily.

It is with respect to these and other considerations that the disclosure made herein is presented.

SUMMARY OF THE INVENTION

According to an aspect of the present invention, a method is provided for uniquely identifying weld joints of a pipeline structure. In particular, the method comprises applying at each of a plurality of weld joints, two distinguishable circular patterns representing a latitude and a longitude of a given weld joint, respectively. More specifically, each of the patterns comprises a plurality of concentric circular bands divided into a plurality of radial sectors and each radial sector represents a respective digit in a numerical sequence. Moreover, each section of a circular band represents a value of a corresponding digit, and a respective central circle of the circular patterns represents a sign (+/−). The method further comprises the step of including, for each of the plurality of weld joints, respective numerical values of the latitude and the longitude for the given weld joint in an encoded format by shading sections within the respective circular patterns according to an encoding scheme.

According to other aspects of the present invention, a system is provided for uniquely identifying weld joints of a pipeline structure. The system comprises a global position sensor configured to be placed in proximity to each of a plurality of weld joints and respectively measure a numerical value of latitude and longitude. The system also comprises a computing device including a computer readable storage medium, a communication interface, a processor that is in operative communication with the communication interface, the storage medium and the position sensor and software modules stored on the storage medium and executable by the processor. In particular, the software modules include a code generation module that, when executed, configures the processor to encode a numerical value for longitude and latitude for a given weld joint within two distinguishable circular patterns respectively representing the longitude and latitude of the given weld joint. More specifically, each of the circular patterns and comprises a plurality of concentric rings divided into a plurality of radial sectors, wherein each sector represents a respective digit in a numerical sequence, and wherein each section of a circular band represents a value of a corresponding digit, and wherein a central circle represents a sign (+/−). In addition, the code generation module further configures the processor to encode the numerical values for longitude and latitude within the circular patterns according to an encoding scheme specifying particular sections of the respective circular patterns that are to be marked.

The system further comprises one or more code application devices that are configured to apply the two distinguishable circular patterns on or near the given weld joint using a contrast material that is capturable in a digital radiographic image captured during inspection of the given weld joint. In addition, the one or more code application devices are configured to selectively deposit the contrast material in the particular sections of the respective patterns as specified by the processor executing the code generation module.

These and other aspects, features, and advantages can be appreciated from the following description of certain embodiments of the invention and the accompanying drawing figures and claims.

DETAILED DESCRIPTION OF CERTAIN EMBODIMENTS OF THE INVENTION

In one or more embodiments, systems and methods are provided for physically labeling structural features with pattern-based codes that uniquely identify respective features. The disclosed systems and methods are also provided for inspecting the structural features and identifying the features based on the pattern-based codes. In one non-limiting practical example further described herein, the systems and methods for labeling and identifying features are used to facilitate monitoring the structural condition of weld joints connecting sections of pipe in a pipeline structure and, more specifically, to verify that on-site inspection of each weld joint in the pipeline was properly performed.

According to a salient aspect, the weld joints are labeled with information suitable for identifying respective weld joints. Preferably, the identifying information is encoded using a visual pattern-based coding scheme. For instance, in an exemplary embodiment, the identifying information includes the geographic latitude and longitude coordinates of a given weld joint, which are encoded using two distinguishable circular patterns that correspond to latitude and longitude, respectively. Representing information specific to the weld joint as a visual, or at least machine readable, pattern-based code can be beneficial in that the code can be captured with the inspection apparatus yet is not easily understood and forged by a technician performing the inspection. Moreover, by encoding a numerical value specific to the weld joint using one or more circular patterns provides the added benefit of maximizing the information density per unit of area. For clarity, the term "code" or "pattern-based code" is intended to refer to a visual representation of identification information encoded within a pattern according to the exemplary encoding schemes further described herein.

According to a further salient aspect, preferably each pattern-based code is applied to the surface of the pipe on or near a respective weld joint using a contrast material such that the code is revealed in image of the weld joint that is captured during inspection. Accordingly, the imagery can be analyzed to identify the inspected weld joints for the purpose of verifying that each weld joint was properly inspected (e.g., imaged by the technician) in the field during a subsequent inspection.

Figure 1:
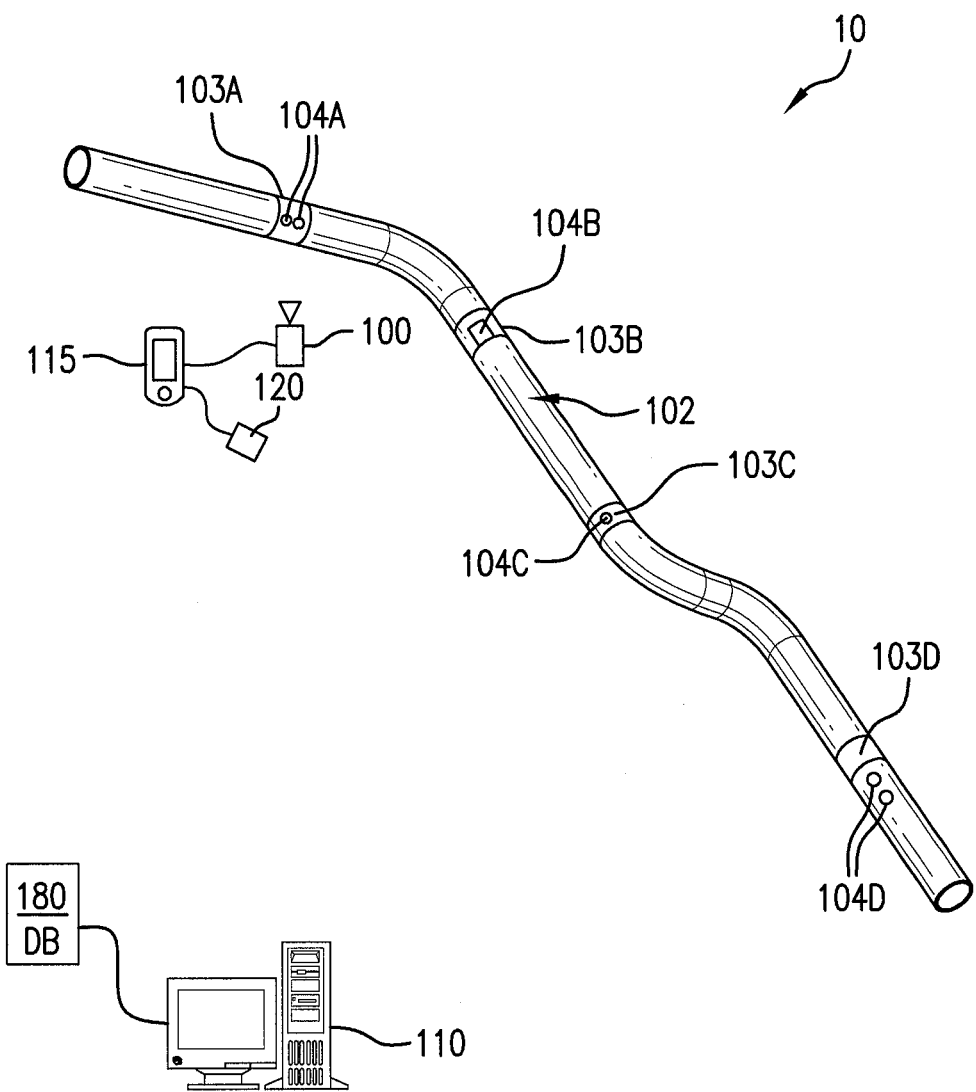
FIG. 1 is a diagram illustrating an exemplary system for uniquely identifying pipe welds according to an embodiment of the present invention.

FIG. 1 is a high-level diagram illustrating a system for uniquely identifying pipe welds 10 in accordance with one or more of the disclosed embodiments. As shown the system can include an inspection apparatus 100 that is used for inspecting the pipeline 102 comprising multiple weld joints 103A-103D. In the exemplary application disclosed herein, the inspection apparatus is a radiographic imaging device, which is commonly used to inspect the structural condition of pipelines and weld joint. Other types of inspection apparatuses can be used as well, for example and without limitation, optical inspection devices, which are also known in the art.

As further shown in FIG. 1, the weld joints can each be labeled with one or more pattern-based codes 104A-104D that are applied on or in proximity to each weld joint. Preferably each code is positioned relative to a given weld joint such that the code can be imaged using the inspection device 100 during inspection of the weld joint. Accordingly, the imagery can be analyzed to read the code and identify the weld joint for the purpose of verifying proper inspection of the weld joints in the pipeline (e.g., ensuring that all weld joints in the pipeline were properly inspected). For example, multiple circular pattern-based codes 104D can be applied in close proximity to the weld joint 103D such that a routine scan of the weld joint using the inspection apparatus 100 reveals the codes within the inspection image(s) and without requiring any additional imaging steps. By way of further example, a single circular pattern-based code 104C can be applied on at least a portion of the weld joint 103C.

Accordingly, the inspection apparatus 100 can be arranged with various computer hardware and software components that serve to enable operation of the inspection device and, in addition, perform operations relating to the analysis of the information captured by the inspection device. The analysis of the inspection imagery captured using the inspection device, such as the analysis of any codes therein, can also be performed using a separate computing device that receives the images from the inspection apparatus 100 over a data communication connection (not shown). For instance, the analysis of the information can be performed using a remote computing device 110 and/or a computing device 115 located in the field during inspection.

Preferably, each code is applied to the surface being inspected in a way that it cannot be separated from the structure and replaced by another label. For instance, a code application device 120 can be configured to selectively deposit paint onto the surface of the pipeline so as to replicate the visual pattern of a given code. According to a salient aspect, the codes are preferably applied to the surface of the pipeline 102 using a contrast material such that the codes are revealed in the output generated by the inspection device 100 during inspection of the weld joint. For instance, the contrast material can be a substance that scatters x-ray photons so the code is revealed in the digital radiographic image of the weld joint captured using inspection device 100, such as a substance including lead. By way of further example, in applications in which optical inspection technologies are used, the contrast material can be a substance that reflects the particular radiation emitted and captured by the optical inspection device during inspection.

According to a further salient aspect, the weld joints are preferably labeled with information suitable for distinguishing between the weld joints according to a visual pattern-based coding scheme. As noted, visually encoding information specific to the weld as a visual pattern can be preferable because the information can be captured with the inspection apparatus and is machine readable yet is not easily understood or forged by a technician performing the inspection.

In one or more exemplary embodiments, the information used to identify a given weld joint can include numerical geographical coordinate values. Because geographical coordinates can be very precise in identifying the position of a weld joint, and can easily be determined accurately in the field during or after installation, such information is suitable for uniquely identifying a particular weld joint. For example, geographical coordinates represented with six (6) decimal digits identify a location with a precision of 11 cm. While geographic coordinates represented with five (5) decimal digits can be enough to identify a weld joint, the exemplary embodiments described herein use six (6), as this provide an order of magnitude more precision with only one extra digit. However, a numerical value including more or less decimal digits can be coded utilizing the same methodology proposed herein for different applications.

It should be understood that one or more numerical value(s), of any type of identification scheme, can be used to identify a particular weld joint without departing from the scope of the disclosed embodiments. However, it can be preferable to label weld joints according to the geographic coordinates, as measured in the field. This approach eliminates the need to rely upon any existing identifiers which uniquely identify the weld joints such as previously assigned identifiers for respective weld joints or the pipe sections joined by respective weld joints. In other words, the process of determining the geographic location of a given weld joint, generating and applying the code for the given weld joint, entirely in the field, facilitate verifying proper inspection in the future and without having to pre-define weld-joint identifiers or record and track any existing identifiers during the installation process. Moreover, in the event that ordinary wear in the field causes a code applied to a weld joint be unreadable or incomplete, a code can be generated and reapplied to the weld joint using a re-measured geographic location. Accordingly, the application of a newly generated code can, in some embodiments, be performed without regard to any previously recorded identification information for the weld joint or the previously generated code. In addition or alternatively, the new code can be generated as a function of the previously recorded identification information, say, by cross-referencing the re-measured location with the originally measured location to ensure that the new code matches the original code to a prescribed degree of accuracy (e.g., is the same code representing the exact same coordinates, or falls within an acceptable margin of error relative to the original code and location).

In the exemplary embodiment further described herein, the latitude coordinate is represented by ten (10) numerical digits, consisting of nine digits plus a North/South indicator digit. The longitude coordinate is represented by nine (9) numerical digits, consisting of eight (8) digits plus an East/West indicator digit. Furthermore, these numerical values for latitude and longitude, respectively, can be represented using two distinct circular pattern templates 300. For example, FIG. 2A depicts two exemplary pattern templates 200, wherein the pattern 210 is used to represent longitude and the pattern 250 is used to represent latitude.

Figure 2A:
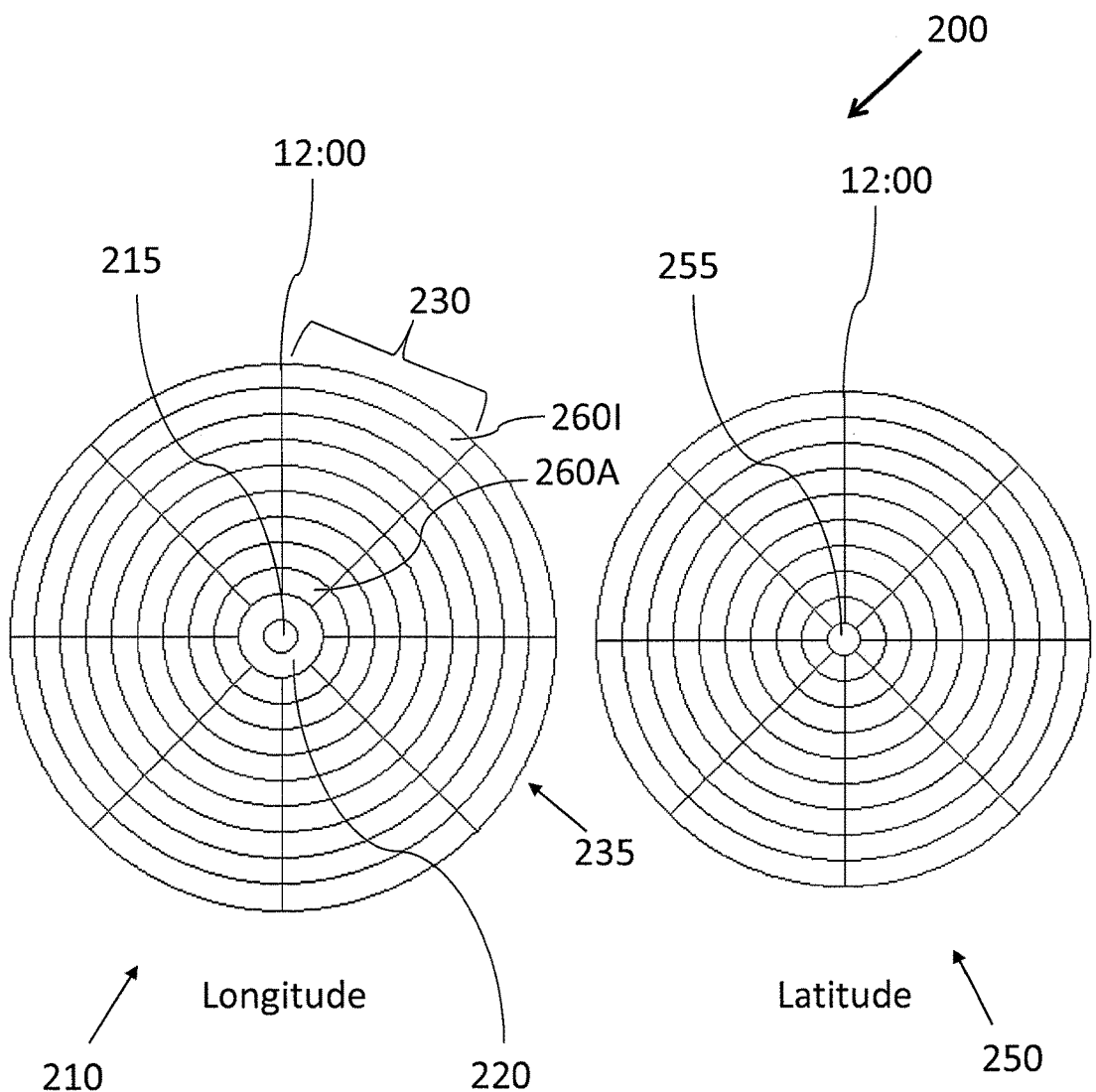
FIG. 2A is a diagram illustrating two exemplary distinguishable circular patterns for conveying encoded information according to an embodiment of the present invention.

The pattern templates 200 shown in FIG. 2A are empty or, in other words, are devoid of encoded location information. The values of the longitude and latitude coordinates can be represented in a respective pattern by shading (e.g., darkening, painting or filling in) or otherwise including markings which are selectively deposited in certain sections of the respective pattern (dots, hatching, etc.) according to the encoding scheme further described below (more generally, "shading"). As noted, representing numerical values using a circular pattern provides the benefit of maximizing the information density per unit of area.

The empty patterns 200 are both characterized as having concentric rings or "bands" at different radial distances from the center. The primary difference between the two patterns is in the central portion of the patterns. In particular, the central portion of the longitude pattern 210 includes two concentric circles in the center, namely, center circle 215 and a surrounding ring 220. The central portion of the latitude pattern 250 comprises one circle 255. Accordingly, the patterns can be distinguished during inspection and analysis based on such features. In both patterns, a plurality of concentric rings surround the central portion and are divided by radial lines extending from the central portion to the outer edge of the pattern. As shown, the radial lines are provided at respective angles thereby defining an even number of radial sectors. For example, radial sectors 230 and 235, among the eight total radial sectors of pattern 210, are expressly identified in FIG. 2A. In addition, the radial lines divide the circular rings such that each radial sector comprises nine segments referred to as "trapezoidal segments." For instance, among the nine trapezoidal segments that define radial sector 230 of pattern 210, the innermost segment 260A and the outermost segment 260I of sector 230 are expressly identified and the intervening trapezoidal segments (e.g., segments 240B-260H) are omitted for simplicity.

In an exemplary embodiment, the numerical value for longitude and latitude can be represented by shading various regions of patterns 210 and 250, respectively, according to the following convention:

In both patterns, the circle in the center (e.g., circle 215 and 255) can represent the sign of a coordinate, namely, positive (+) or negative (−). In particular, the center circle represents a positive sign (+) when it is darkened and a negative sign (−) when it is un-shaded. In the case of the longitude pattern 210, a shaded center 215 (e.g., a positive sign) represents the direction West and an unshaded center 215 represents the direction East. In the case of the latitude pattern 250, a shaded center 255 can represent the direction North and the unshaded center can represent the direction South.

The large concentric circular ring 220 surrounding center circle 215 in the longitude pattern 210, when darkened, can represent a longitude value beyond 99° West or 99° East. Because latitude coordinates do not exceed 90° such a circle is not present in the latitude pattern 250.

As noted above, the rings surrounding the central portion of both patterns are divided into eight (8) radial sectors and each radial sector includes nine (9) trapezoidal segments.

Each radial sector represents one of the eight (8) remaining digits defining the coordinate. More specifically, by comparing the pattern to a clock face, the radial sector after the 12 o'clock position (when read in the clockwise direction) corresponds to the first digit. The remaining digits are respectively represented by the subsequent radial sectors, when considered in a clockwise manner. For example, the sector 230 of the longitude pattern 210 represents the first digit and the sector after the 3 o'clock position, sector 235, represents the first decimal digit of the coordinate.

The nine (9) trapezoidal segments within a given radial sector represents the numerals one (1) through nine (9) starting from closest to the center portion of the pattern. For example, segment 260A of sector 230 represents the numeral one (1) and segment 260I represents the numeral nine (9).

Figure 2B:
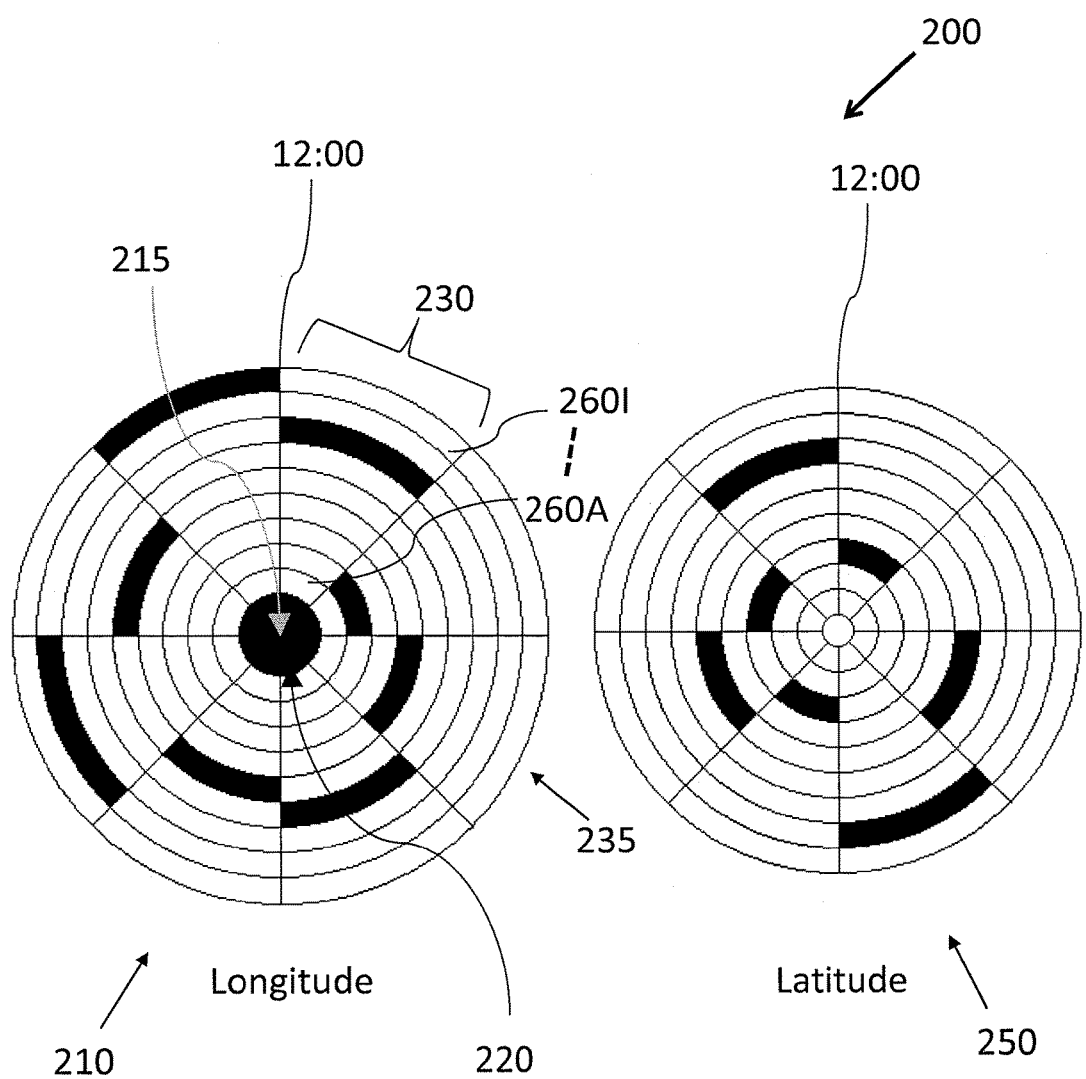
FIG. 2B is a diagram illustrating the circular patterns of FIG. 2A encoded with information according to an embodiment of the present invention.

For example, FIG. 2B illustrates the coordinates longitude: +172.465859 and latitude: −30.583537 expressed on the circular patterns of FIG. 2A according to the aforementioned scheme.

While generating codes based on the geographic coordinates of the weld joints and using two distinguishable visual patterns can be preferable, the disclosed embodiments can similarly be used to encode other numerical identifier(s) that are assigned to uniquely identify a particular weld joint according to other numbering and identification conventions. For example, the foregoing exemplary encoding scheme can be used to represent any numerical value in a similar way, where each radial sector corresponds to a respective parameter (e.g., a position of a number in an order) and the darkening of a trapezoidal section within a particular sector represents a respective parameter value (e.g., numerical value between 1 and 9).

Figure 3:
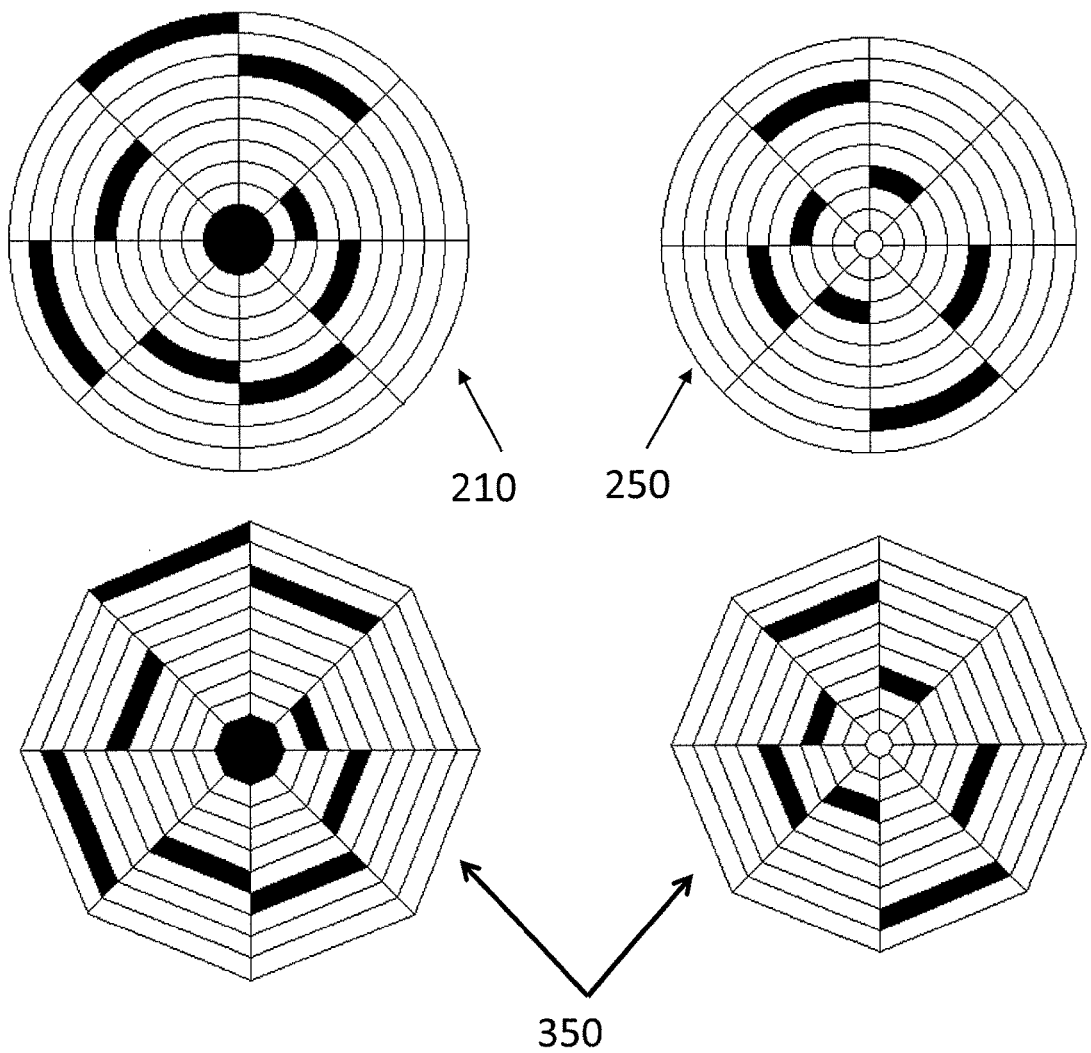
FIG. 3 is a diagram illustrating exemplary encoded patterns for conveying identification information according to an embodiment of the present invention.

Patterns having other shapes can similarly be used to encode numerical information according to the foregoing scheme. For instance, FIG. 3 illustrates octagonal patterns 350 encoded according to the convention described in relation to FIGS. 2A-2B. In particular, the coordinates longitude: +172.465859 and latitude: −30.583537 are expressed as the two distinguishable circular patterns 210 and 250 (as shown in FIG. 2B) as well as two distinguishable octagonal patterns 350.

The exemplary encoded coded patterns can of FIG. 3 can be decoded to determine the coordinates as follows.

Starting from the longitude pattern on the left, the circle in the middle is darkened, which corresponds to + or Longitude West.

The second circle from the center is also darkened, which corresponds to longitudes above 99° West, so the longitude starts with +1.

The first triangular sector, which is directly after the 12 o'clock position in a clockwise direction, corresponds to the number seven (7), as the seventh trapezoid from the center is darkened.

The next triangular sector corresponds to the number two (2).

The third triangular sector, which represents the first decimal digit, corresponds to the number four (4).

According to the same principle the remaining sectors represent the numbers 65859, respectively.

Accordingly, the complete Longitude value represented by both the octagonal and circular patterns on the left of FIG. 3 is +172.465859.

The same principle can be used to decode the latitude coordinate expressed in the circular and octagonal patterns shown on the right in FIG. 3. More specifically, the central circle is empty, which corresponds to a "−" (i.e., a latitude South). The first triangular sector corresponds to a three (3). The second triangular sector has no trapezoid darkened, which corresponds to a zero (0) and so on. Accordingly, the complete latitude coordinate represented by both the octagonal and circular patterns on the right of FIG. 3 is −30.583537.

Figure 4A:
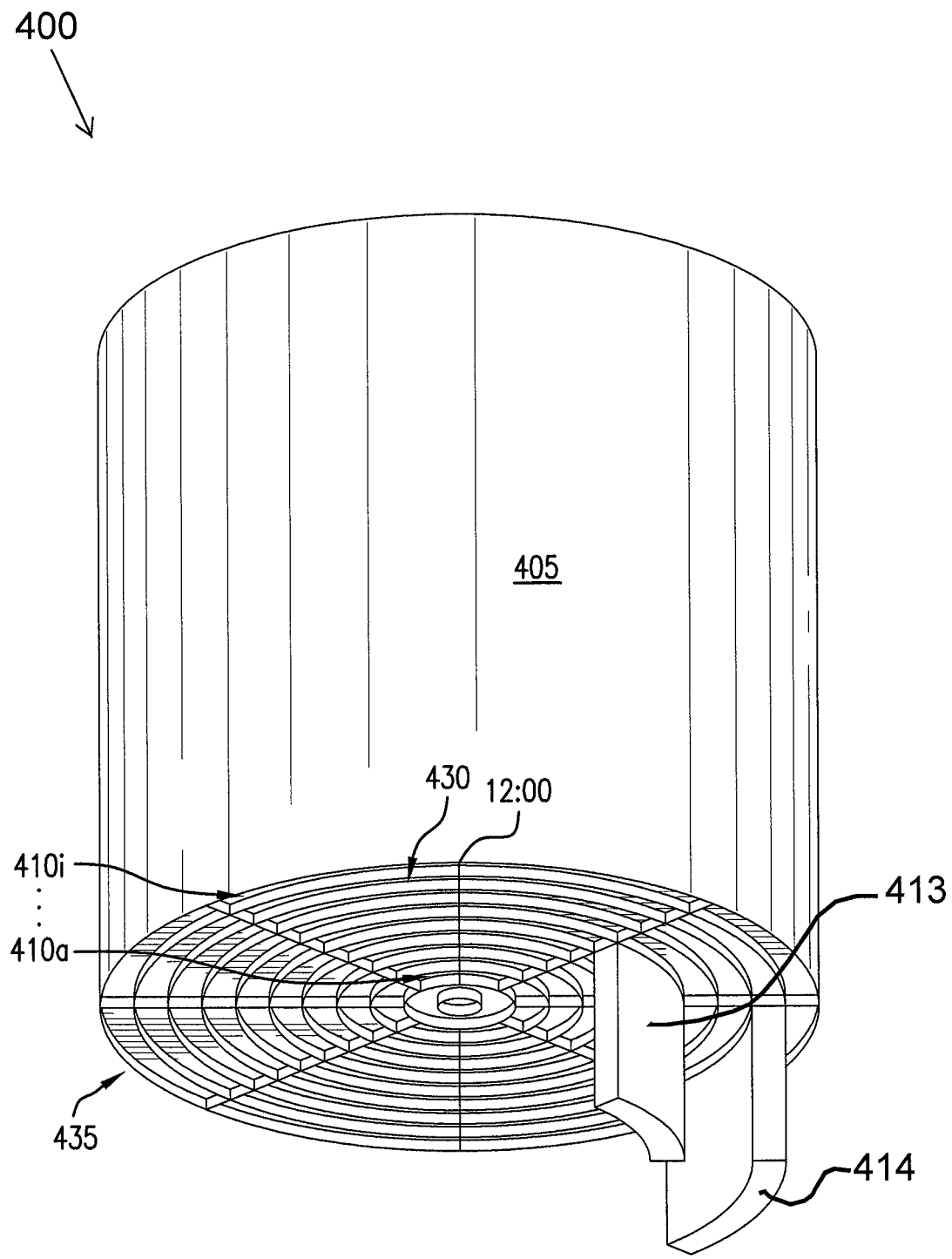
FIG. 4A is a perspective view illustrating an exemplary device for applying a pattern-based code on a surface of a structure according to an embodiment of the present invention.
Figure 4B:
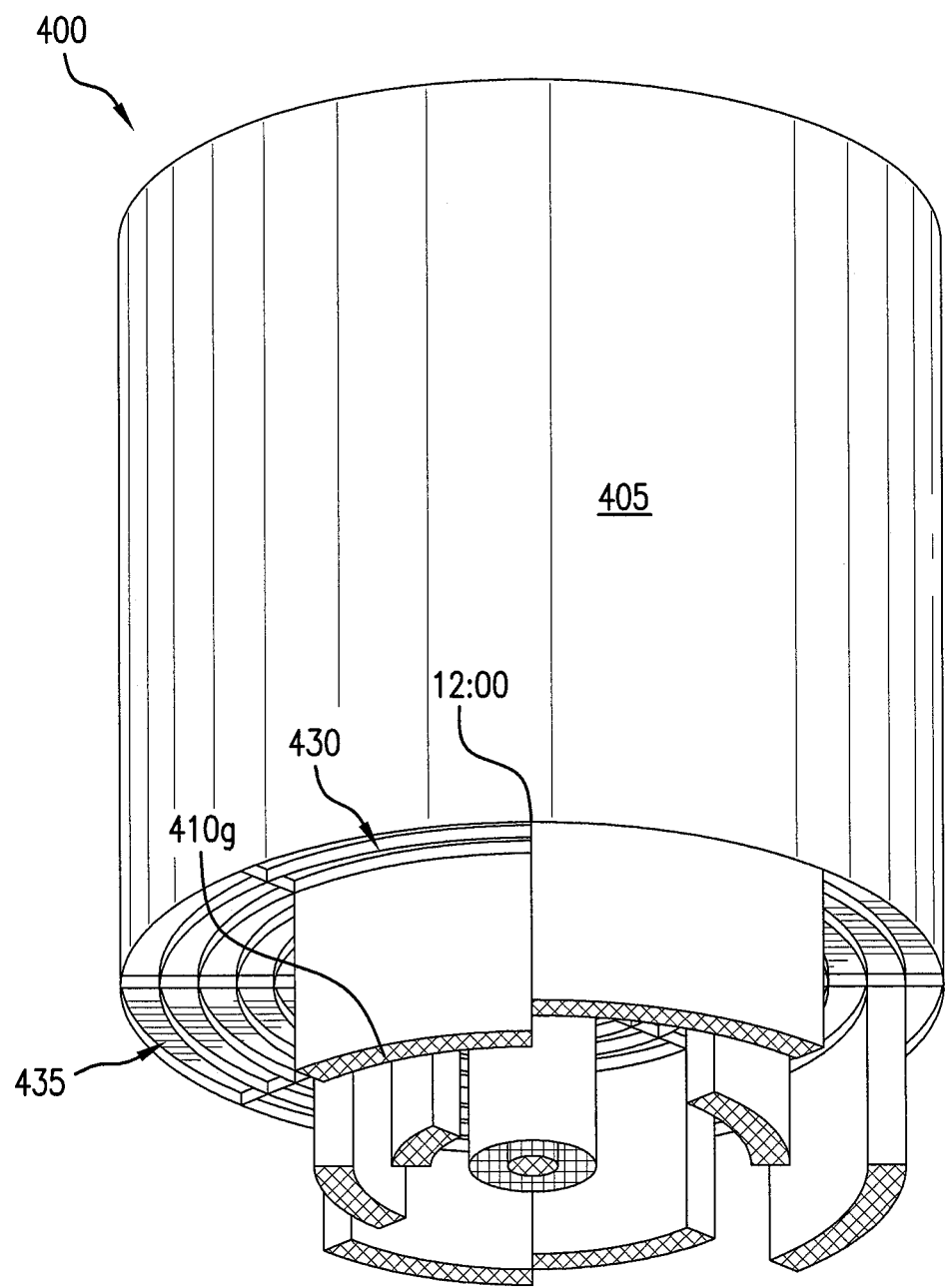
FIG. 4B is a perspective view of the exemplary code application device of FIG. 4A according to an embodiment of the present invention.
Figure 4C:
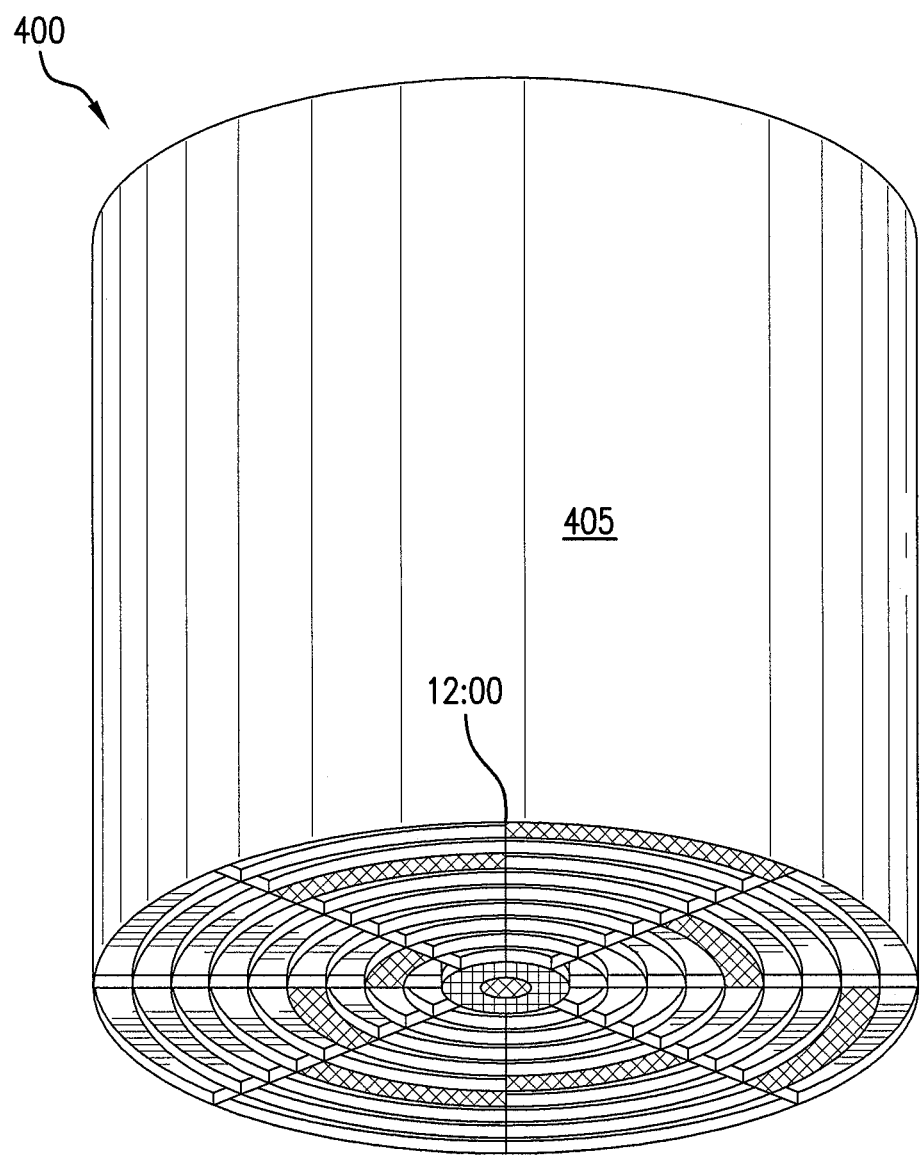
FIG. 4C is a perspective view of the exemplary code application device of FIG. 4A according to an embodiment of the present invention.

As noted, a code application device 120 can be used to physically mark the surface of the pipeline 102 shown in FIG. 1 with the codes. FIGS. 4A-4C provide a more detailed diagram of exemplary configurations of a code application device 400 for applying the codes onto the surface of a pipe. As shown, the code application device comprises a generally cylindrical body 405 surrounding an interior volume and containing a plurality of retractable slabs. The retractable slabs correspond to the portions of a given pattern template that are selectively shaded to convey a code comprising a visual pattern. Thus, it can be appreciated that the shape and relative position of respective slabs held within the body 405 depends on the particular shape of the pattern template and coding convention. For example and without limitation, the particular code application device 400 shown in FIGS. 4A-4C is configured to apply codes generated according to the longitude circular pattern template 210 and corresponding encoding convention described in connection with FIGS. 2A-2B. For reference, the 12:00 o'clock reference position of the longitude pattern 210 is shown in FIGS. 2A and 2B and the corresponding 12:00 o'clock reference position on the code application device 400 is also shown in FIGS. 4A-4C.

As shown, the interior volume of the housing 405 can be divided into compartments that each correspond in size, shape and position to the radial sectors of pattern 210. In particular, sectors 430 and 435 correspond, respectively, to sectors 230 and 235 of the longitude pattern 210 shown in FIG. 2A. Each radial sector can be configured to include nine (9) individual compartments holding respective slabs therein that respectively correspond to the radial trapezoidal segments within a given radial sector. For example, slabs 410a-410i identified in FIG. 4A, shown as being withdrawn into respective compartments of sector 430, can correspond to the trapezoidal segments 260A-260I of sector 230 shown in FIG. 2A. For simplicity, in FIG. 4A, two of the radial sectors are illustrated as each having one slab (slabs 413 and 414) exposed, while the remaining slabs and the circular central regions of the longitude pattern 210 are shown as being retracted within their respective compartments.

Preferably the slabs, such as, slabs 410a-410i, are configured slide up and down within respective compartments of the body 405. In some automated configurations, the code application device 400 can include a programmable controller/processor that is coupled to motors or actuators within the housing (not shown) that are configured to independently expose the slabs or retract them within the housing in response to instructions received from a control computer/processor. Accordingly, the programmable controller, using the motors or actuators, can be configured to selectively move the slabs such that only slabs that correspond to a generated code for application onto a surface extend beyond the bottom end of the housing 405. Preferably, the code application device 400 is also configured to include a locking mechanism (not shown) that maintains the slabs in the designed position so as to allow the device to be used to apply the encoded pattern to the surface.

In some embodiments, the on-board controller/processor can be configured to receive, as an input, a particular numerical value to be encoded and applied to the structure, say, longitude: +172.465859 or latitude: −30.583537. The controller can also be configured to translate the numerical value into the corresponding encoded pattern format. In addition or alternatively, the controller can be in wired or wireless communication with another computing device that measures the GPS location, translates the location data into the encoded pattern format and communicates instructions causing device 400's on-board controller to selectively move the slabs into the appropriate position.

As a result of the selective positioning of the slabs in order to apply the code onto the surface, only certain slabs will stick out from the bottom of the device. For example, FIG. 4B shows the slabs corresponding to the shaded sections of longitude pattern 210 being exposed, while the remaining slabs are shown as being retracted within their respective compartments. As shown, only slab 410g, among the slabs 410a through 410i, is extending beyond the bottom end of the housing 405, whereas the other slabs in sector 430 are retracted within the interior of the housing 405.

In some embodiments, another code application device that is analogous to the exemplary code application device 400 can be used to generate and apply the latitude pattern 250 shown in FIG. 2A. In addition or alternatively, the code application device 400 can be configured to be adjustable and useable to apply multiple different patterns (e.g., both longitude pattern 210 and latitude pattern 250).

In order to transfer a code onto the pipe, an image of a given pattern is preferably applied to the surface of the pipe using a contrast material. For instance, in radiography, the contrast material can be any substance containing a heavy element such as but not limited to lead.

As an example of a suitable process for transferring the pattern onto the pipe, the bottom end of the code application device 400, which has slabs selectively exposed in the shape of a particular code, can be dipped in a lead based paint, provided either in a sponge or as a liquid layer. The bottom end of the code application device 400 can then be applied onto the surface of the section of pipe proximate to the weld joint (or whatever object is to be labeled) so as to transfer paint onto the surface in the shape of the code. It should be understood that the code application device 400 can be configured to mark the encoded pattern on the surface, one or more portions of the template (e.g., the borders that define the various sections of the template that are filled in or left unfilled to convey the encoded information), or a combination of the foregoing. For instance, FIG. 4C shows the code application device 400 arranged such that the slabs corresponding to the shaded sections of longitude pattern 210 are extended such that they are flush with the bottom ends of the inner walls that define the compartments and that correspond to the longitude pattern 210, while the remaining slabs are shown as being retracted within their respective compartments. Accordingly, the bottom end of the code application device can be dipped in paint and used to transfer the longitude pattern template 210 and the code onto the surface of the pipe.

In addition or alternatively, the slabs can be made of a hard metal material and used to cut or emboss the pattern onto a segment, piece, or slab of existing contrast material. It can be appreciated that one or more of the exemplary embodiments, the code can be applied as a positive image, wherein the presence of contrast material in a particular section conveys information, or a negative image, wherein the absence of contrast material conveys the information, and can be read accordingly.

Figure 5A:
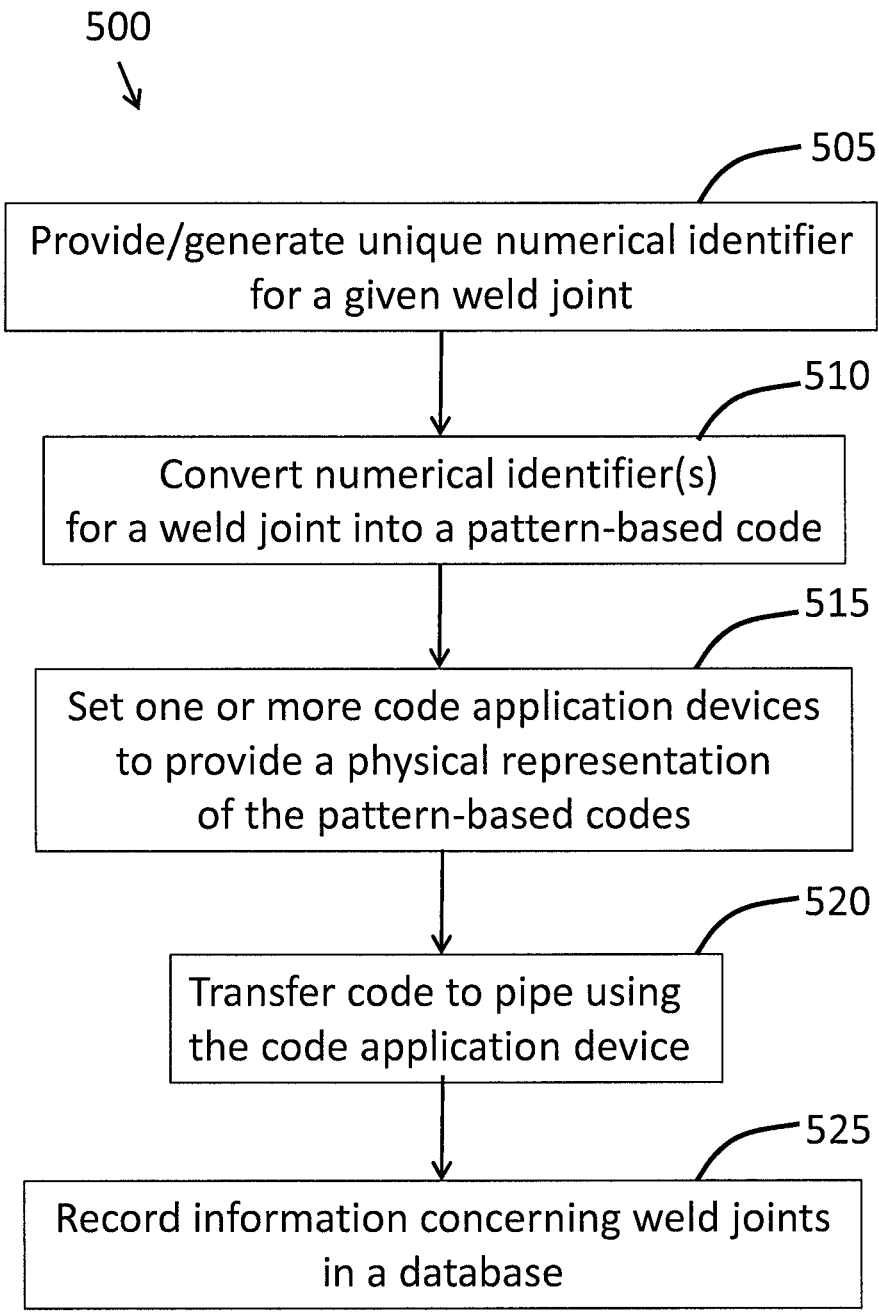
FIG. 5A is a flow chart of a method for generating pattern-based codes and applying the codes to a surface of a structure according to an embodiment of the present invention.
Figure 5B:
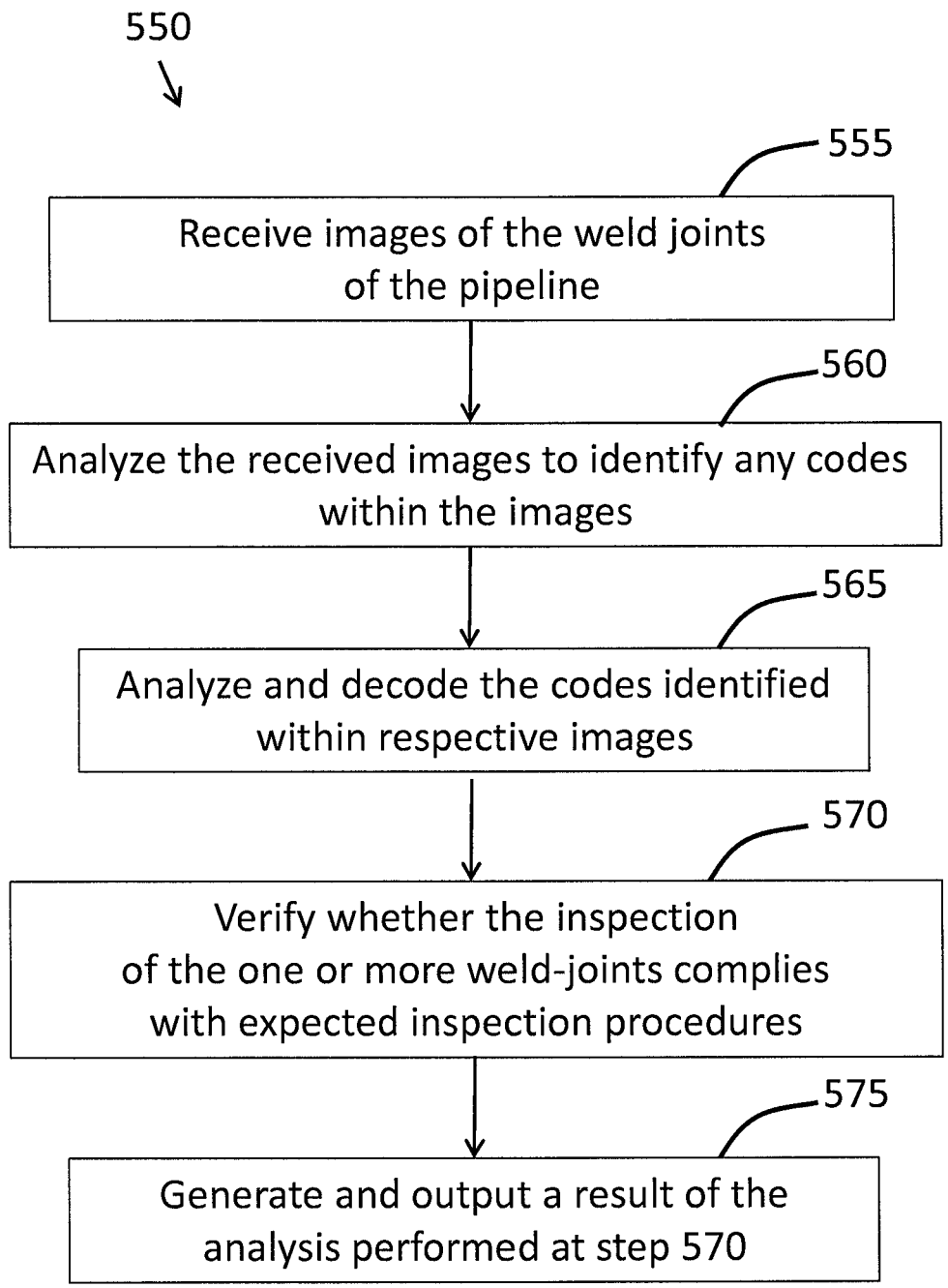
FIG. 5B is a flow chart of a method for inspecting and analyzing pattern-based codes applied to a surface of a structure according to an embodiment of the present invention.

FIG. 5A is a flow chart of a method 500 for generating unique codes for pipe welds and labeling pipe welds according to one or more embodiments of the present invention. FIG. 5B is a flow chart of a method 550 for analyzing the inspection images of the weld joints to verify that each weld joint was properly inspected, according to an embodiment of the present invention. As a non-limiting practical example, methods 500 and 550 are further described herein with continued reference to the system 10 of FIG. 1, the encoding scheme shown in FIG. 2A-2B and the exemplary marking device 120 shown and described in connection with FIG. 4A-4B.

In step 505, the method 500 begins by providing a unique numerical identifier for a given weld joint such as geographic coordinate(s) of the given weld joint. For instance, during installation of the pipeline structure 102 shown in FIG. 1, a technician in the field can carry a hand-held computing device 115 having an on-board GPS sensor to measure the geographic longitude and latitude coordinates for each of the pipe welds to the desired degree of accuracy.

In step 510, the numerical identifier(s) for the given weld joint is converted into a pattern-based code. For instance, the processor of the hand-held device 115, which is configured by executing software modules in the form of executable instructions, can be configured translate the numerical longitude and latitude coordinates for the given pipe weld into a respective code based on the patterns and encoding rules described in connection with FIGS. 2A-2B. As noted, according to a salient aspect, the codes are generated using two, preferably distinguishable, circular patterns, wherein one pattern represents latitude and the other pattern represents longitude. According to a further salient aspect, each of the patterns can comprise a plurality of concentric rings divided into a plurality of radial sectors, wherein each sector represents a respective digit in a numerical sequence and wherein each section of a circular ring represents a value of a corresponding digit, and wherein a central circle represents a sign of the encoded value (+/−).

In step 515, one or more code application devices are set to provide a physical representation of the pattern-based codes generated at step 515 respectively. For example, in an exemplary automated configuration of the code application device 120, the hand-held device 115 can transmit information describing a generated code representing the latitude of the given weld joint to the code application device 100 over a wired or wireless connection. In response, the controller of the code application device 100 can interpret the received information and, using the actuators, selectively extend or retract the slabs of the code application device such that only slabs corresponding to the received code extend beyond the bottom end of the housing 405.

By way of further example, in configurations where the slabs of the code application device 120 are manually set into position by the technician, the hand-held device 115 can be configured to visually output the generated code, for instance, using an associated display, such that the technician can view the pattern and set the corresponding slabs of the code application device 120 accordingly.

Then, at step 520, the code is transferred to the surface of the pipe using the code application device 120. More specifically, preferably, the image of the code can be applied to the surface of the pipe using a contrast material that appears in the imagery captured by the inspection device during inspection of the labeled weld joint. This provides the benefit of the identification code being captured passively and seamlessly during inspection of the weld joint without requiring the code to be imaged or read separately from the inspection process. For instance, in radiography, the contrast material can be any substance containing a heavy element, such as but not limited to lead, that appears in radiographic imagery captured of the weld joint during inspection.

As an example of a suitable process for transferring the pattern onto the pipe, the bottom end of the code application device 120, which has slabs selectively exposed in the shape of a particular code, can be dipped in a lead based paint, either in a sponge or as a liquid layer. The bottom end of the code application device 120 can then be applied onto the surface of the section of pipe proximate to the weld joint so as to transfer paint onto the surface and selectively deposit the paint in the shape of the code. The application device 120 can optionally undergo cleaning to remove any remaining contrast material after each application to a weld joint.

It should be understood that the code application device 120 can be configured to mark the encoded pattern on the surface, one or more portions of the template (e.g., the borders that define the various sections of the template that are filled in or left unfilled to convey the encoded information), or a combination of the foregoing. Accordingly, in cases where contrast material is applied to the surface in the shape of the pattern/template pattern and selectively deposited within certain sections of the pattern (e.g., to convey the encoded information), the steps of applying the pattern and selectively depositing contrast material within sections of the pattern can be performed contemporaneously or as separate steps.

It should also be understood that steps 515 and 520 can be repeated to apply any number of additional codes to the given weld joint such as the generated code representing the latitude of the given weld joint. In addition, the application of the one or more codes to a particular weld joint can be performed according to any number of parameters that facilitate subsequent inspection of the weld joints. For instance, the codes can preferably be applied on or within a prescribed distance of the weld joint and a prescribed distance from one another to facilitate contemporaneous imaging of the codes and the weld joint.

In connection with generating and applying the codes on the weld joints of the pipeline 102, according to steps 505-520, at 525, information concerning each weld joint can be recorded in a database 180 by one or more of the hand-held device 115 and the control computer 110. For instance, the measured GPS location and the corresponding codes that are generated to identify a given weld joint can be transmitted from the hand-held device 115 for storage in the database 180 maintained by the control computer 110. Accordingly, the information stored in the database can be available and referenced during subsequent inspection activities.

FIG. 5B is a flow diagram of a method 550 for analyzing the inspection images of the weld joints in pipeline 102 and verifying that the weld joints have been properly inspected. As further described herein, the steps of method 550 are described as being performed by the control computer 110 of system 10. It should, however, be understood that one or more steps of method 550 can similarly be performed by other computing devices such as the inspection apparatus 100 and the hand-held device 115, or any combination of one or more of the foregoing devices.

In step 555, the method begins by receiving images of the weld joints of the pipeline 102. The images of the weld joints can be received at the control computer 110 as one or more individual images or batches of images. Accordingly, depending on the implementation, the images can be received contemporaneously with inspection of the pipeline structure (e.g., in near-real time) or after inspection of one or more sections of the pipeline structure has been completed. Furthermore, the image analysis and steps for verifying proper inspection further described herein can be performed by the control computer 110 contemporaneously with or subsequent to the inspection of the pipeline 102.

In step 560, the one or more received images are analyzed by the control computer 110 to identify any codes that are present within the images. More specifically, the processor of the control computer, which is configured by executing software modules comprising instructions in the form of code, can analyze an image of a weld joint and identify the portions of the image that corresponds to a code. For instance, the configured processor can utilize image processing and feature recognition algorithms to identify any regions within the image that include one or more codes in the shape of a circular pattern.

In step 565, codes identified within respective images are analyzed and decoded. More specifically, the processor of the control computer 110, which is configured by executing software modules comprising instructions in the form of code, can be configured to determine, based on known distinguishing features of the templates representing longitude and latitude (e.g., templates 210 and 250 of FIG. 2A-2B), which of the codes detected within a given image represents a longitude coordinate and which represents a latitude coordinate. In addition, based on the determination that a code represents a longitude coordinate, the configured processor can decode the information presented in the code according to the particular set of rules described in connection with FIGS. 2A-2B. The configured processor can similarly decode the identified codes representing the latitude coordinate.

In step 570, the configured processor can verify whether the inspection of the one or more weld-joints complies with expected inspection procedures based on the identified longitude and latitude coordinates for one or more of the weld joints and known information concerning the weld joints stored in the database 180. More specifically, the processor of the control computer 110, which is configured by executing software modules comprising instructions in the form of code, can be configured to cross-reference the decoded longitude and latitude coordinates for a given weld joint with the known longitude and latitude coordinates of respective weld joints in the pipeline 102 stored in the database 180. In addition, the configured processor can determine whether the given weld joint has been previously inspected during the current inspection cycle and annotate a record in the database accordingly. For instance, if the weld joint has not been inspected during the current inspection cycle the record can be updated to indicate the weld joint has been inspected. Alternatively, if the weld joint was already inspected, the weld joint can be flagged in the record as having been inspected multiple times. Repeated inspection of a weld joint is just one example of potentially improper inspection activity that can be detected using the control computer and flagged. It should be understood that the processor can be configured to detect other types anomalous activity based on the identification of weld joints from the inspection imagery and with reference to the information maintained in the database. For instance, the processor can be configured to verify that the weld joints are being inspected in an order that is generally consistent with the path of the pipeline (e.g., starting from location A and moving generally toward location Y) or consistent with previous inspection cycles.

In connection with the verification step, the control computer 110 can also be configured to analyze additional information provided to the control computer 110 along with the inspection images such as metadata gathered by the inspection device 100 during inspection. For instance, the control computer can analyze time-stamps for a series of inspection images of respective weld joints in view of the decoded locations of the weld joints to determine whether the timing of the images is consistent with the relative locations of the weld joints and a typical pace that weld joints are inspected. By way of further example, the metadata associated with an inspection image of a given weld joint can include a GPS location measured by the inspection device while imaging the particular weld joint. Accordingly, the control computer can be further configured to compare the GPS metadata for consistency with the decoded GPS location, as determined from the code within the given inspection image.

In step 575, the configured processor can generate and output a result of the analysis performed at step 570. For instance, the control computer can output a report including alerts describing one or more instances of anomalous inspection activity that are inconsistent with prescribed inspection protocols. By way of further example, the report can identify and provide the location of one or more weld joints that were not inspected properly and can include instructions prompting further inspection of the identified weld joints accordingly. In some embodiments, the report can be output via an associated display of the control computer 110 or other output device. In addition or alternatively, the report can be transmitted for output by one or more other devices such as the hand-held device 115, the inspection apparatus 100 or a remote computing device operated by an inspection supervisor.

It should be understood that in applications where the compliance monitoring is conducted contemporaneously with the inspection in the field, the generated reports can be generated and output so as to provide alerts, feedback and instructions on the inspection in near-real time.

Figure 6:
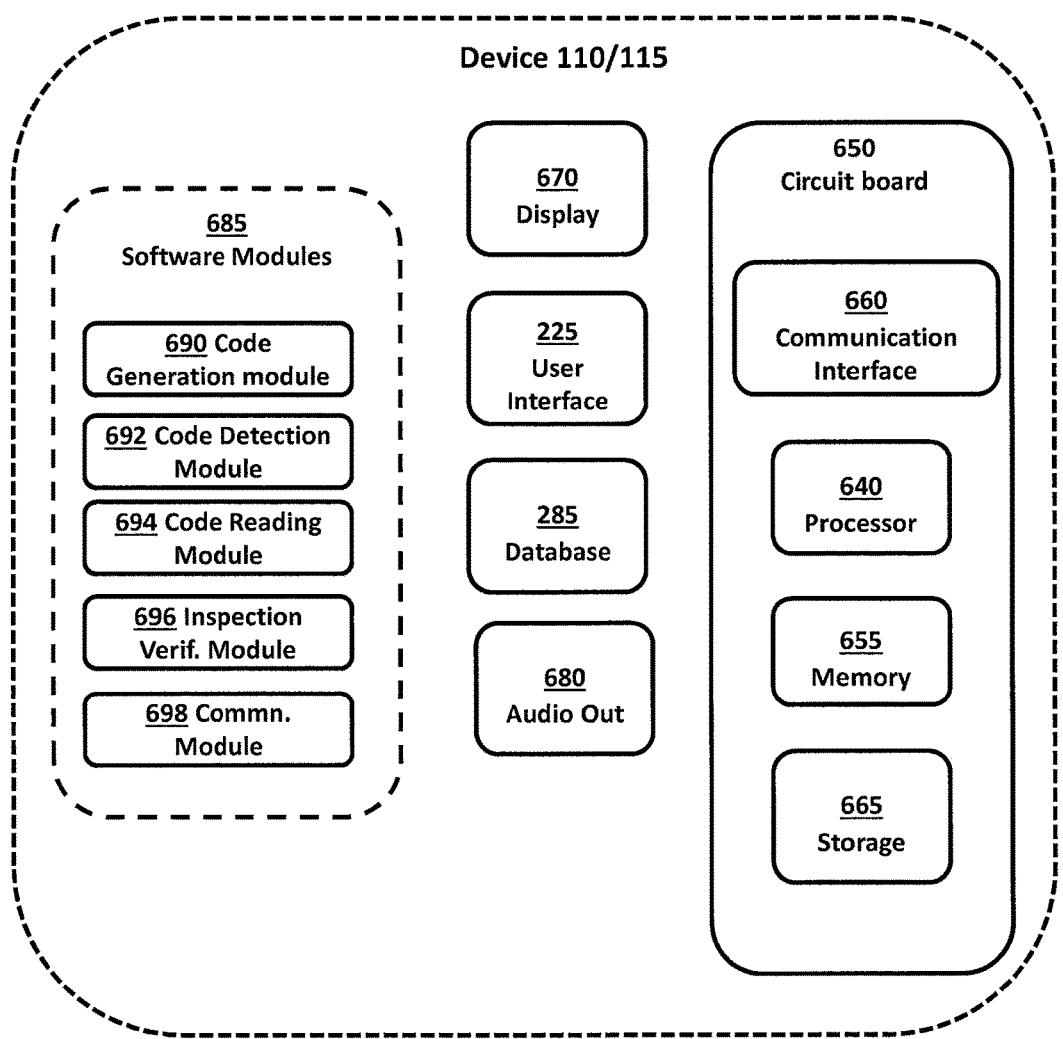
FIG. 6 is a block diagram illustrating exemplary hardware and software components of an exemplary computing device according to an embodiment of the present invention.

FIG. 6 is a block diagram illustrating an exemplary configuration of hardware and software components of one or more of the computing devices (e.g., the control computer 110 and the hand-held computing device 115) described in the present disclosure as performing the various operations relating to the generation of codes, application of codes or the analysis of codes for the purpose of verifying compliance.

Components of the computing devices include a processor 640 and a circuit board 650. The circuit board can include a memory 655, a communication interface 660 and a computer readable storage medium 665 that are accessible by the processor 640. The board 650 can also include or be coupled to a power source (not shown) source for powering the computing device.

The processor 640 and/or circuit board 650 can also be coupled to a display 670, for visually outputting information to an operator (user), a user interface 675 for receiving operator inputs, and an audio output 680 for providing audio feedback as would be understood by those in the art. As an example, the processor 640 could emit a visual signal from the display 670, for instance, the image of a weld joint captured using the inspection apparatus 100, or a code identifying the weld joint that is to be applied to the weld joint. Although the various components are depicted either independent from, or part of the circuit board 650, it can be appreciated that the components can be arranged in various configurations.

The processor 640 serves to execute software instructions that can be loaded into the memory. The processor 640 can be implemented using multiple processors, a multi-processor core, or some other type of processor. The memory 655 is accessible by the processor 640, thereby enabling the processor to receive and execute instructions stored on the memory and/or on the storage. Memory 655 can be implemented using, for example, a random access memory (RAM) or any other suitable volatile or non-volatile computer readable storage medium. In addition, memory 655 can be fixed or removable.

The storage medium 665 can also take various forms, depending on the particular implementation. For example, storage medium 665 can contain one or more components or devices such as a hard drive, a flash memory, a rewritable optical disk, a rewritable magnetic tape, or some combination of the above. The storage medium 665 also can be fixed or removable or remote such as cloud based data storage systems (remote memory or storage configuration not shown). The storage, for example, can be used to maintain the database 180 (shown in FIG. 1), which stores unique identifiers for the labeled features (e.g., measured GPS locations of weld joints), the corresponding codes, information relating to the inspection of the features or other information and or data used or generated while carrying out operations and implementing aspects of the systems and methods disclosed herein.

One or more software modules 685 are encoded in the memory 655 and/or storage medium 665. The software modules can comprise one or more software programs or applications having computer program code or a set of instructions executed in the processor 640. Such computer program code or instructions for carrying out operations and implementing aspects of the systems and methods disclosed herein can be written in any combination of one or more programming languages. While software modules are stored locally in storage 665 or memory 655 and execute locally in the processor 640, the processor can interact with remotely-based computing platform via communication interface 660, and via a local or wide area network to perform calculations or analysis.

During execution of the software modules 685, the processor 640 is configured to perform the various operations of the system for identifying and inspecting weld joints described herein, including without limitation, the previously described steps for generating pattern-based codes that uniquely identify weld joints, applying of the generated codes to the weld joints, analyzing of image data including the pattern-based codes, and verifying the proper inspection of the structures. The software modules can include code for implementing the aforementioned steps and other steps and actions described herein, for example and without limitation: a code generation module 690, which configures the processor to convert a unique numerical identifier to a pattern-based code; a code detection module 692, which configures the processor to identify within the images captured during inspection a portion of the image including a pattern-based code; a code reading module 694, which configures the processor to analyze the pattern-based code to decipher the encoded information and identify the corresponding weld joint; and an inspection verification module 696, which configures the processor to determine whether the inspection of the weld joints in the pipeline was performed according to prescribed protocols and procedures; and a communication module 698, which configures the processor to communicate with remote devices (e.g., the inspection device 100) over a communication connection (not shown) such as a communication network or any wired or wireless electronic communication connection.

The program code of the software modules 685 and one or more of the non-transitory computer readable storage devices (such as the memory 655 and/or the storage 665) can form a computer program product that can be manufactured and/or distributed in accordance with the present disclosure, as is known to those of ordinary skill in the art.

Illustrative embodiments and arrangements of the present systems and methods provide a system and a computer implemented method, computer system, and computer program product for inspecting smart structures. The flowchart and block diagrams in the figures illustrate the architecture, functionality, and operation of possible implementations of systems, methods and computer program products according to various embodiments and arrangements. In this regard, each block in the flowchart or block diagrams can represent a module, segment, or portion of code, which comprises one or more executable instructions for implementing the specified logical function(s). It should also be noted that, in some alternative implementations, the functions noted in the block can occur out of the order noted in the figures. For example, two blocks shown in succession can, in fact, be executed substantially concurrently, or the blocks can sometimes be executed in the reverse order, or one or more of the blocks can be repeated, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts, or combinations of special purpose hardware and computer instructions.

It is to be understood that any structural and functional details disclosed herein are not to be interpreted as limiting the systems and methods, but rather are provided as a representative embodiment and/or arrangement for teaching one skilled in the art one or more ways to implement the methods.

It should be understood that although much of the foregoing description has been directed to systems and methods for physically labeling weld joints of a pipeline with unique identifiers comprising pattern-based codes based on geographic location and analyzing the codes to identify the weld joints based on the codes to enforce compliance with inspection protocols, the systems methods disclosed herein can be similarly deployed in scenarios, situations, and settings beyond the referenced scenarios. For example, any type of structure or feature can be labeled and inspected using the exemplary systems and methods described herein. It should be further understood that any such implementation and/or deployment is within the scope of the system and methods described herein.

It is to be further understood that like numerals in the drawings represent like elements through the several figures, and that not all components and/or steps described and illustrated with reference to the figures are required for all embodiments or arrangements The terminology used herein is for the purpose of describing particular embodiments only and is not intended to be limiting of the invention. As used herein, the singular forms "a", "an" and "the" are intended to include the plural forms as well, unless the context clearly indicates otherwise. It will be further understood that the terms "comprises" and/or "comprising", when used in this specification, specify the presence of stated features, integers, steps, operations, elements, and/or components, but do not preclude the presence or addition of one or more other features, integers, steps, operations, elements, components, and/or groups thereof.

Terms of orientation are used herein merely for purposes of convention and referencing, and are not to be construed as limiting. However, it is recognized these terms could be used with reference to a viewer. Accordingly, no limitations are implied or to be inferred.

Also, the phraseology and terminology used herein is for the purpose of description and should not be regarded as limiting. The use of "including," "comprising," or "having," "containing," "involving," and variations thereof herein, is meant to encompass the items listed thereafter and equivalents thereof as well as additional items.

While the invention has been described with reference to exemplary embodiments, it will be understood by those skilled in the art that various changes can be made and equivalents can be substituted for elements thereof without departing from the scope of the invention. In addition, many modifications will be appreciated by those skilled in the art to adapt a particular instrument, situation or material to the teachings of the invention without departing from the essential scope thereof. Therefore, it is intended that the invention not be limited to the particular embodiment disclosed as the best mode contemplated for carrying out this invention, but that the invention will include all embodiments falling within the scope of the appended claims.

What is claimed is:

1. A method for uniquely identifying weld joints of a pipeline structure, comprising:
   applying at each of a plurality of weld joints, two distinguishable circular patterns representing a latitude and a longitude of a given weld joint, respectively,
      wherein each of the patterns comprises a plurality of concentric circular bands divided into a plurality of radial sectors,
      wherein each radial sector represents a respective digit in a numerical sequence,
      wherein each section of a circular band represents a value of a corresponding digit, and
      wherein a respective central circle of the circular patterns represents a sign (+/−); and
   including, for each of the plurality of weld joints, respective numerical values of the latitude and the longitude for the given weld joint in an encoded format by shading sections within the respective circular patterns according to an encoding scheme.

2. The method of claim 1, wherein the two distinguishable circular patterns are applied and the sections within the respective circular patterns are shaded by selectively depositing a contrast material that is capturable in digital radiographic image during inspection of the given weld joint.

3. The method of claim 2, wherein the two circular patterns are applied within a prescribed spacing from one another.

4. The method of claim 2, further comprising:
   measuring, with a computing device using a global position sensor positioned at the given weld joint, the respective numerical values of latitude and longitude for the given weld joint.

5. The method of claim 2, wherein the including step further comprises:
   converting the numerical values of longitude and latitude, respectively, into the encoded format based on an encoding scheme defining which of the sections within the respective circular patterns are to be shaded using contrast material.

6. The method of claim 2, further comprising:
   recording the respective numerical values of the latitude and the longitude for each of the plurality of pipeline welds in a database.

7. The method of claim 5, further comprising:
   setting a code application device according to the encoded numerical values for longitude and latitude, respectively, and wherein the step of selectively depositing the contrast material within sections of the respective circular patterns is performed using the code application device.

8. The method of claim 6, further comprising:
   providing images of a plurality of inspected weld joints at a control computing device, wherein the images are captured during inspection of the weld joints using an inspection device and subsequent to the applying and including steps;
   analyzing each of the images using the control computing device, the analyzing step including:

detecting, within an image of a given inspected weld joint, a plurality of circular patterns each having a respective plurality of sections shaded using the contrast material;

identifying, among the plurality of detected circular patterns according to prescribed distinguishing features, a circular pattern representing a latitude of the given inspected weld joint and a circular pattern representing a longitude of the given inspected weld joint, and translating, based on the encoding scheme and the identified circular patterns, the respective plurality of shaded sections of the latitude circular pattern and the longitude circular pattern into respective numerical values of the latitude and the longitude for the given inspected weld joint;

comparing, using the control computing device, the translated numerical values for latitude and longitude against one or more of respective latitude and longitude values for the plurality of weld joints stored in the database; and verifying, using the control computing device based on the comparison, whether inspection of the pipeline is being performed according to prescribed inspection procedures; and outputting, using the control computing device, a result of the verifying step.

9. The method of claim 1, wherein the circular pattern representing longitude further comprises a continuous concentric ring surrounding the central circle and wherein the plurality of concentric rings divided into the plurality of radial sectors surround the continuous ring.

10. The method of claim 9, wherein the continuous ring represents a longitude value beyond 99° West or 99° East.

11. The method of claim 1, wherein the applying and including steps are performed contemporaneously.

12. A system for uniquely identifying weld joints of a pipeline structure, comprising:
a global position sensor configured to be placed in proximity to each of a plurality of weld joints and respectively measure a numerical value of latitude and longitude;
a computing device comprising:
  a computer readable storage medium;
  a communication interface,
  a processor in operative communication with the communication interface, the storage medium and the position sensor, and
  software modules stored on the storage medium and executable by the processor, wherein the software modules include:
    a code generation module that, when executed, configures the processor to encode a numerical value for longitude and latitude for a given weld joint within two distinguishable circular patterns respectively representing the longitude and latitude of the given weld joint,
      wherein each of the circular patterns and comprises a plurality of concentric rings divided into a plurality of radial sectors, wherein each sector represents a respective digit in a numerical sequence, and wherein each section of a circular band represents a value of a corresponding digit, and wherein a central circle represents a sign (+/−), and
      wherein the numerical values for longitude and latitude are encoded within the circular patterns according to an encoding scheme specifying particular sections of the respective circular patterns are to be marked; and
    one or more code application devices configured to apply the two distinguishable circular patterns on or near the given weld joint using a contrast material suitable for presenting in digital radiographic image captured during inspection of the given weld joint, and selectively deposit the contrast material in the particular sections of the respective patterns as specified by the processor configured by executing the code generation module.

13. The system of claim 12, further comprising:
a database; and
a database module, among the software modules, that configures the processor to record the respective numerical values of the latitude and the longitude each of the plurality of the weld joints in a database.

14. The system of claim 13, further comprising:
a control computing device comprising a processor configured by executing one or more software modules including:
  a communication module that, when executed, configures the control computing device processor to receive images of the plurality of weld joints at the control computing device, wherein the images are captured during inspection of the weld joints using an inspection device;
  a code analysis module that, when executed, configures the control computing device processor to detect, within an image of the given weld joint, a plurality of circular patterns each having a respective plurality of sections shaded using a contrast material, identify, among the plurality of circular patterns according to prescribed distinguishing features, a circular pattern representing the latitude of the given weld joint and a circular pattern representing the longitude of the given weld joint, and translate, based on the encoding scheme, the respective plurality of shaded sections of the latitude circular pattern and the longitude circular pattern into the respective numerical values of the latitude and the longitude for the given weld joint, and
  an inspection verification module that, when executed, configures the control computing device processor to compare the translated numerical values for latitude and longitude against one or more of respective latitude and longitude values for the plurality of weld joints stored in the database, verify, based on the comparison, whether inspection of the pipeline is being performed according to prescribed procedures and output a result of the verification.

15. The system of claim 12, wherein the circular pattern representing longitude further comprises a continuous concentric ring surrounding the central circle and wherein the plurality of concentric rings divided into the plurality of radial sectors surround the continuous ring.

16. The method of claim 15, wherein the continuous ring represents a longitude value beyond 99° West or 99° East.

17. The system of claim 12, wherein the code application device is configured to apply a respective circular pattern and selectively deposit the contrast material in the particular sections of the respective circular pattern contemporaneously.

* * * * *